United States Patent [19]

Metters

[11] Patent Number: 4,915,765
[45] Date of Patent: Apr. 10, 1990

[54] METHOD OF MANUFACTURING A FLUID BARRIER FOR MEDICAL DRESSING

[75] Inventor: John R. Metters, Hingham, Mass.

[73] Assignee: Aegis Medical Corporation, Weymouth, Mass.

[21] Appl. No.: 147,371

[22] Filed: Jan. 20, 1988

Related U.S. Application Data

[63] Continuation-in-part of Ser. No. 93,502, Sep. 19, 1987, Pat. No. 4,829,995.

[51] Int. Cl.⁴ .............................................. B32B 31/18
[52] U.S. Cl. ..................................... 156/267; 156/290; 156/291; 188/156; 604/304; 604/307
[58] Field of Search ............ 156/267, 290, 291, 306.3, 156/289; 15/209 R; 604/289, 304, 307; 401/207; 128/132 R, 156; 215/227, 232; 220/269, 270, 359; 428/47, 48, 66, 78, 121, 124, 126, 127, 194, 198, 211

[56] References Cited

U.S. PATENT DOCUMENTS 3,709,763  1/1973  O'Neil .............................. 156/291
3,784,998  1/1974  Jones ................................ 15/209 R
4,650,705  3/1987  Ghodsian .......................... 128/156

Primary Examiner—Caleb Weston
Attorney, Agent, or Firm—Lahive & Cockfield

[57] ABSTRACT

Disclosed is a barrier for medical dressings which is impervious to blood or other body fluids. The barrier may be joined or pre-attached to the top surface of a medical dressing. The dressing may then be handled by the barrier and applied to a wound. The barrier prevents blood and other body fluids from penetrating the dressing and contacting a health care worker or other individual who may be treating the patient. A method for manufacturing the barriers for medical dressings is also disclosed.

2 Claims, 2 Drawing Sheets

METHOD OF MANUFACTURING A FLUID BARRIER FOR MEDICAL DRESSING

BACKGROUND OF THE INVENTION

This application is a continuation-in-part of U.S. patent application Ser. No. 093,502 entitled "Fluid Barrier for Medical Dressing", filed Sept. 4, 1987, now U.S. Pat. No. 4,829,995.

The present invention is directed to fluid barriers for medical dressings and the method of manufacturing such barriers. More particularly, the invention is directed to a medical dressing having an outer barrier which is impervious to body fluids.

Recently there has been concern over the risk of contacting infectuous diseases such as AIDS through contact with tainted blood or other body fluids. Doctors, nurses, medical technicians and other persons in the health care field form a group which faces a particularly high risk of contacting such diseases. It is known, for example, that the AIDS virus, as well as other harmful bacteria and viruses, may be transmitted through contact with medical dressings, syringes, and the like, which bear contaminated blood or body fluids. Health care professionals may contact life-threatening diseases through contact with such items.

The risk of contacting potentially fatal diseases can be greatly reduced by providing bandages and dressings with a protective barrier impervious to blood and body fluids. Convential gauze bandages and other dressings do not lessen the risk of infection posed to health care workers. When such absorbent dressings are placed over as wound, blood often penetrates the dressing. Health care workers treating a patient may then be exposed to bacteria and viruses through contact with the soiled dressing. Thus, there exists a need to provide additional protection to health care workers by limiting their potential for exposure to such bacteria and viruses.

Accordingly, it is an object of the present invention to provide a medical dressing having one side which is impervious to the passage of blood and other body fluids. Another object of the invention is to provide a fluid-impermeable material which may be adhesively secured to a conventional medical dressing. A further object of the invention is to provide a dressing or apparatus which is easily and safely handled. It is an additional object of the invention to provide an efficient, economical method of manufacturing such a dressing. Other objects of the invention will be apparent to those of ordinary skill in the art upon reading the present disclosure.

SUMMARY OF THE INVENTION

The present invention comprises a fluid-impermeable barrier material which may be adhesively secured to a conventional medical dressing, such as a bandage or gauze pad, to form a shield which protects a health care worker from exposure to blood or body fluids if they penetrate the dressing. The barrier comprises a substrate which may be made of plastic, paper or other suitable materials impervious to fluids. One side of the substrate contains an adhesive coating, which is likewise substantially impermeable, and may be used to affix a bandage or dressing to the barrier material. A strip of foil may be disposed between the substrate and the adhesive layer to form a more effective barrier. In addition, a top side of the substrate may include an upwardly protruding tab, which may be integral with the barrier material, to provide a means for easily handling the dressing.

In one embodiment, a dressing may be adhered to the barrier once the adhesive layer is exposed. With the dressing firmly secured to a barrier a health care worker may grasp the barrier material and apply the dressing to a wound. The barrier will prevent blood and body fluids from coming into contact with skin of the health care worker. When the dressing is no longer needed it may be removed by grasping the tab and discarded.

In another embodiment of the invention, dressings and bandages may be manufactured with a pre-secured barrier.

In another aspect of the invention, a method is disclosed for manufacturing medical dressing barriers which are adhered to a strip of release paper. According to the method, a web of barrier substrate material with a protective base layer of silicon release paper is supplied to a manufacturing line. A tab-forming substrate material having discrete patches of a permanent adhesive, separated by substantially equally sized adhesive-free patches is likewise supplied to the manufacturing line and is joined to the top surface of the barrier substrate material to form a medical dressing barrier stock. A tab element able to protrude from the top surface of the medical barrier is formed by the portion of the tab-forming substrate which lacks adhesive. Following the application of the tab-forming substrate to the barrier substrate, the resulting stock is then advanced to a downstream cutting station.

At the cutting station, a die cuts the stock material to form medical barriers of a desired shape. As part of the cutting operation, a portion of the tab element is shortened by a trimming operation. Following this cutting operation the waste substrate material surrounding the barriers is removed, yielding a multitude of discrete barriers adhered to a continuous length of release paper. The release paper, with the attached barriers, preferably is collected by a take-up roll. Subsequently, the barriers (and release paper) may be repackaged into smaller rolls or strips.

In another embodiment, the tab element may be folded in the direction opposite that of its natural orientation, following the step of cutting the substrate material to the desired shape. This enables the tab element naturally to protrude from the top surface of the substrate, rather than to lie flush against the substrate.

DETAILED DESCRIPTION OF THE INVENTION

Figure 1:
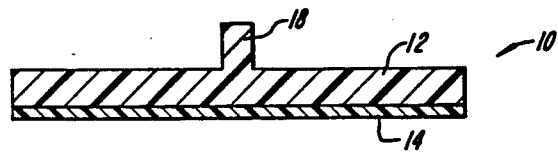
FIG. 1 is a schematic cross section of one embodiment of the medical dressing barrier of the present invention.

As shown in FIG. 1, the medical dressing barrier 10 of the present invention includes a fluid-impermeable substrate material 12 and an adhesive layer 14. In another embodiment of the invention, illustrated in FIG. 2, a foil strip 16 is disposed between the substrate material 12 and the adhesive layer 14. In addition, the embodiments of FIGS. 1 and 2 each include a tab means 18 which protrudes from a top surface of the substrate material. Tab means 18, which may be integral with the substrate, functions as a handle which facilitates convenient and safe handling of the dressing barrier 10.

Figure 2:
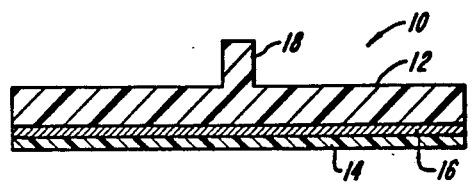
FIG. 2 is a schematic cross section of another embodiment of the medical dressing barrier of the present invention.
Figure 3:
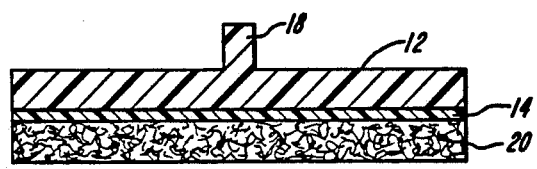
FIG. 3 is a schematic cross section of the medical dressing barrier of FIG. 1 having a medical dressing attached thereto.
Figure 4:
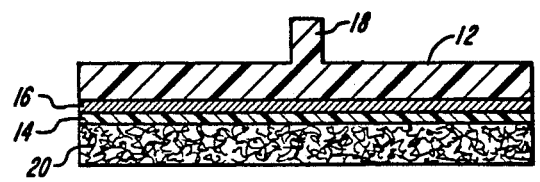
FIG. 4 is a schematic cross section of the medical dressing barrier of FIG. 2 having a medical dressing affixed thereto.

FIG. 3 illustrates another embodiment of the invention whereby the dressing barrier 10 of FIG. 1 has a dressing 20 adhered thereto. FIG. 4 illustrates the barrier 10 of FIG. 2 with a dressing 20 adhered thereto. The embodiments of FIGS. 3 and 4 may either be manufactured in such a way that the dressing 20 is pre-secured to the barrier 10, or the barrier 10 may be manufactured separately and subsequently joined to a dressing 20 prior to use.

The substrate material 12 of the present invention may be constructed from virtually any material of suitable strength which is acceptable for pharmaceutical and medical applications. In a preferred embodiment, the substrate comprises a flexible material. The substrate should also be of such a quality that it is impervious to blood and other body fluids. In addition, the substrate should have affixed to one of its sides an adhesive material, such as an acrylic adhesive, which is suitable for pharmaceutical and medical applications. The medical dressing material 20 of the present invention may be of any type of bandaging, gauze or dressing material known in the art.

In a preferred embodiment of the invention, the substrate material is manufactured from 50 pound paper known as Silverback Pharmaceutical Paper, manufactured and sold by Fasson Company. This material includes a permanent pressure sensitive acrylic-based adhesive 14, known as S-727, which is affixed to the bottom of substrate 12. The preferred substrate material includes a thin layer of foil 16 which is disposed between the substrate and the adhesive in order to provide additional protection from fluid leakage. In this embodiment, it is believed that the medical dressing barrier is totally impervious to blood and other body fluids.

Other preferred substrate materials which are equally useful include the 50 pound Pharmaceutical Hi-gloss Facestock and 50 pound Pharmaceutical Lithofacestock, both of which are manufactured and sold by Fasson Company. While these substrate materials lack a foil layer 16, they both provide excellent protection against the passage of fluids.

In one embodiment, the medical dressing barriers of FIGS. 1 and 2 may be sold separately and subsequently affixed to a medical dressing just prior to use of the dressing. In this embodiment, a health care worker would remove a protective strip (not shown) covering the adhesive layer and then handle the barrier 10 by tab 18 to secure the barrier 10 to a bandage or dressing of a corresponding size. The adhesive layer 14 would enable the barrier 10 to firmly and securely grasp and retain the dressing. The dressing could then be applied to the wound while pressure is applied through the barrier 10. The dressing may be safely removed from the patient by grasping the barrier 10 (which still retains the dressing) through tab 18 and disposing the entire unit. In this way, the health care worker is not exposed to any blood or bodily fluid which may have penetrated the dressing.

In another embodiment of the invention, the medical dressing barrier 10 may be provided with a pre-attached dressing or bandage of a corresponding size, as shown in FIGS. 3 and 4. In this embodiment, the dressing can simply be applied to a wound by grasping the barrier 10 through tab 18.

Figure 5:
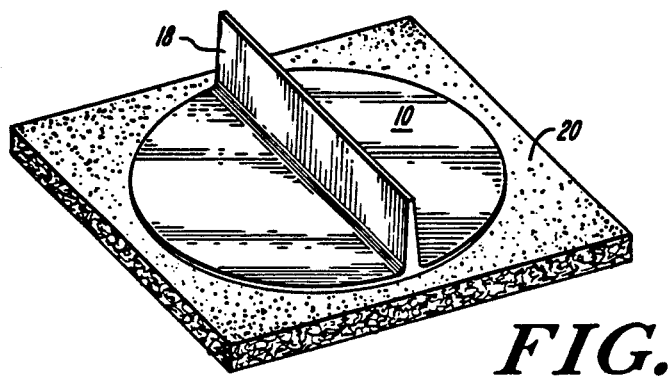
FIG. 5 is a perspective view of a medical dressing barrier of the present invention affixed to a medical dressing.

FIG. 5 illustrates the medical barrier 10 adhered to a dressing material 20. The entire unit may be handled by tab 18.

Figure 6:
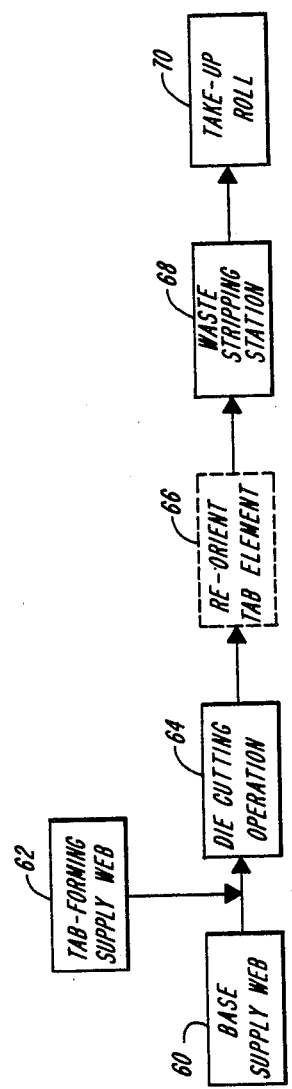
FIG. 6 is a flow chart illustrating the steps of manufacturing a medical dressing barrier according to the present invention.

Provided in FIG. 6 is a flow chart depicting the steps involved in a method of manufacturing the medical dressing barriers according to the present invention. A barrier substrate material 60, of the type described above, is supplied, typically in roll form. The material preferably has an adhesive material on its bottom surface which is protected by and secured to a silicon release paper backing. The adhesive material which joins the substrate to the release paper preferably is a pressure sensitive acrylic based adhesive of the type described above. Although this adhesive securely joins the substrate to the release paper, the substrate may be easily removed when desired. In the preferred manufacturing process the substrate material and joined release paper is continuously fed from a supply roll through a pair of nip rolls, or similar structures able to advance the material from the supply roll to downstream processing stations.

A supply roll of a tab-forming substrate material 62 is positioned somewhat downstream of substrate material 60. Tab-forming substrate 62 comprises a material which is the same as or similar to the barrier substrate material described above. This material is adhered to a silicon release paper by discrete patches of adhesive material in such a way that it may be easily separated from the release paper when desired. A continuous length of the tab-forming substrate material 62 is directed through appropriate guiding and advancing mechanisms such that the release paper is separated from the tab-forming substrate. The tab-forming substrate is deposited on the top surface of the barrier substrate material just after the release paper is stripped from the tab-forming substrate. The tab-forming substrate material is deposited directly over and in alignment with the top surface of the barrier substrate material to form a medical dressing barrier stock material such that portions of tab-forming material adhesively secured to the top surface of the barrier substrate alternate with non-adhered portions of the tab-forming material.

Next, the stock material is advanced downstream to die cutting station 64 which cuts the continuous length substrate stock into a multitude of barrier devices of a desired shape. Preferably, the barriers are of a circular shape, having a diameter of, for example, about 1¾ inches. As the barriers are cut to a desired shape, the die may also shorten the portion of the tab-forming substrate which lacks adhesive. This results in the formation of a tab element which, because it lacks adhesive, may protrude about ⅜ inch from the top surface of the medical barrier. Preferably, the cutting apparatus cuts only the substrate material and does not penetrate the release paper.

Optionally, the manufacturing operation may include a processing station 66 which, following the cutting operation, bends the tab element in a direction opposite that of its natural orientation. This enables the resulting tab element to be more prominent and consquently more easily grasped when the barrier must be utilized.

During the die cutting operation described above, the medical barrier stock material is cut, but the release paper remains intact. Following this cutting operation waste stock material remains adhered to the release paper surrounding the cut medical barriers. The waste stock material is subsequently stripped from the release paper at waste stripping station 68. This results in a multitude of discrete medical barriers being adhered to the release paper. Subsequently, the release paper, with the attached barrier devices, is collected on a take-up roll 70. In post-manufacturing operations the barrier devices and the release paper may be packaged into smaller rolls or into strips of material.

Alternatively, the medical dressing barriers of the present invention may be manufactured from a single sheet of barrier substrate material. According to this embodiment the medical dressing barrier sheet can be adhesively-backed and supplied to an apparatus which crimps a central portion of the sheet to form a tab element of about ⅜ inch in height which is integral with the medical dressing barrier sheet. The adhesive backing of the sheet enables the two portions of the sheet which form the tab to remain permanently adhered. Subsequently, the sheet may be placed On a sheet of release paper and the tab element may be pressed into a position such that it lies flush with the top surface of the barrier.

One of ordinary skill in the art may easily devise a manufacturing line, and the various elements thereof, which facilitates the method of manufacturing described above. It is, of course, understood that a variety of devices and arrangements may be utilized in an automated manufacturing operation embodying the method of this invention.

It is also understood that the apparatus of the present invention may be provided in a variety of shapes and sizes depending on the requirements of a particular application. In addition, other variations or modifications to the apparatus and method of manufacturing the apparatus of the present invention may be made by one having ordinary skill in the art without departing from the scope of the present invention.

What is claimed is:

1. A method of manufacturing a barrier for a medical dressing, comprising the steps of providing a sheet stock of base substrate material having an adhesive layer on one side and disposed on a release paper substrate;

superimposing on the other side of said base substrate a tab-forming substrate to form a medical dressing barrier stock material, said tab forming substrate having non-adhesive backed areas comprising a tab-forming element and adhesive backed areas;

cutting the medical dressing barrier stock material to the desired size and shape and simultaneously trimming a portion of the tab-forming element to provide medical barrier dressings having an adhesive layer on one surface thereof and non-adhered tab members protruding from the other surface;

trimming the waste substrate material surrounding the produced medical dressing barriers from the release paper to yield a multitude of discrete medical dressing barriers adhered to the release paper; and collecting the medical dressing barriers and release paper on a wind-up roll.

2. The method of claim 1 further comprising the step of folding the tab-forming element in a direction opposite to that of its natural orientation, following the step of cutting the medical barrier to its desired shape.

* * * * *